United States Patent
Ambuhl et al.

(10) Patent No.: US 6,767,555 B2
(45) Date of Patent: Jul. 27, 2004

(54) PHARMACEUTICAL COMPOSITIONS

(75) Inventors: Michael Ambuhl, Mohlin (CH); Barbara Lückel, Lorrach (DE); Barbara Haberlin, Riehen (CH); Armin Meinzer, Buggingen (DE)

(73) Assignee: Novartis AG, Basel (CH)

( * ) Notice: Subject to any disclaimer, the term of this patent is extended or adjusted under 35 U.S.C. 154(b) by 66 days.

(21) Appl. No.: 10/217,732

(22) Filed: Aug. 13, 2002

(65) Prior Publication Data

US 2002/0188134 A1 Dec. 12, 2002

Related U.S. Application Data

(63) Continuation of application No. 09/579,372, filed on May 26, 2000, now Pat. No. 6,432,445.

(30) Foreign Application Priority Data

May 28, 1999 (GB) .............................................. 9912476

(51) Int. Cl.⁷ ................................................. A61K 9/48
(52) U.S. Cl. ........................ 424/455; 424/451; 424/452; 424/456
(58) Field of Search ................................ 424/455, 451, 424/452, 456, 463, 454, 453, 457

(56) References Cited

U.S. PATENT DOCUMENTS

| | | | |
|---|---|---|---|
| 4,567,161 A | 1/1986 | Posanski et al. ............... 514/23 |
| 5,110,606 A | 5/1992 | Geyer et al. ................ 424/489 |
| 5,266,590 A | 11/1993 | Narayanan ................. 514/531 |
| 5,300,529 A | 4/1994 | Narayanan ................. 514/788 |
| 5,342,625 A | 8/1994 | Hauer et al. ................ 424/455 |
| 5,389,688 A | 2/1995 | Narayanan ................. 514/788 |
| 5,583,105 A | 12/1996 | Kovacs et al. ................ 514/11 |
| 5,639,724 A | 6/1997 | Cavanak ....................... 514/11 |
| 5,741,512 A | 4/1998 | Hauer et al. ................ 424/450 |
| 5,866,159 A | 2/1999 | Hauer et al. ................ 424/450 |
| 5,916,589 A | 6/1999 | Hauer et al. ................ 424/450 |
| 5,932,243 A | 8/1999 | Fricker et al. ............... 424/450 |
| 5,962,014 A | 10/1999 | Hauer et al. ................ 424/450 |
| 5,962,017 A | 10/1999 | Hauer et al. ................ 424/450 |
| 5,980,939 A | 11/1999 | Kim et al. ................... 424/455 |
| 6,007,840 A | 12/1999 | Hauer et al. ................ 424/450 |
| 6,024,978 A | 2/2000 | Hauer et al. ................ 424/450 |
| 6,028,067 A | 2/2000 | Hong et al. ................. 514/200 |
| 6,063,762 A | 5/2000 | Hong et al. .................. 514/11 |
| 6,432,445 B1 * | 8/2002 | Ambuhl et al. ............. 424/455 |

FOREIGN PATENT DOCUMENTS

| | | |
|---|---|---|
| DE | 3 315 805 | 11/1984 |
| DE | 4 337 041 | 5/1995 |
| DE | 19537836 | 4/1997 |
| EP | 387 647 | 9/1990 |
| EP | 694 308 | 1/1996 |
| EP | 712 631 A2 | 5/1996 |
| EP | 670 715 | 5/1997 |
| EP | 793 966 | 9/1997 |
| EP | 801 130 | 10/1997 |
| FR | 2 609 631 | 1/1987 |
| FR | 2 636 534 | 3/1990 |
| GB | 1 300 516 | 12/1972 |
| GB | 2 228 198 A | 8/1990 |
| GB | 2278 780 A | 12/1994 |
| JP | 06293633 | 10/1994 |
| WO | 96/13273 | 5/1966 |
| WO | 92/13454 | 8/1992 |
| WO | 93/00809 | 1/1993 |
| WO | 94/13777 | 6/1994 |
| WO | 95/08983 | 4/1995 |
| WO | 95/22343 | 8/1995 |
| WO | 96/16132 | 5/1996 |
| WO | 96/36316 | 11/1996 |
| WO | 97/09964 | 3/1997 |
| WO | 97/36610 | 10/1997 |
| WO | 98/33512 | 8/1998 |
| WO | 98/40051 | 9/1998 |
| WO | 98/40094 | 9/1998 |
| WO | 99/00002 | 1/1999 |
| WO | 99/29316 | 6/1999 |
| WO | 99/29335 | 6/1999 |
| WO | 00/40219 | 7/2000 |
| WO | 00/72867 | 12/2000 |

OTHER PUBLICATIONS

Siebenbrodt and Keipert, Eur. J. Pharm. Biopharm., vol. 39(1), pp. 25–30.

Narayanan et al., "N–Alkyl Pyrrolidone Requirement for Stable Water–Based Microemulsions," ASTM Spec. Tech. Publ., 1146, 12, pp. 85–104.

* cited by examiner

Primary Examiner—James M. Spear
(74) Attorney, Agent, or Firm—Thomas R. Savitsky; John D. Thallemer

(57) ABSTRACT

This invention provides composition comprising a cyclosporin and a carrier medium.

14 Claims, No Drawings

PHARMACEUTICAL COMPOSITIONS

This application is a continuation of U.S. patent application Ser. No. 09/579,372, filed May 26, 2000 now U.S. Pat. No.: 6,432,445, which is herein incorporated by reference.

The present invention relates to novel galenic compositions, e.g. substantially oil-free, galenic compositions containing a cyclosporin as an active agent and also comprising a plurality of alkanols.

Cyclosporins present highly specific difficulties in relation to administration generally and galenic compositions in particular, including in particular problems of stability, drug bioavailability, and variability in inter- and intra-patient dose response. The present invention allows the production of a particularly convenient form, namely a capsule. The present invention provides in one aspect a cyclosporin composition in the form of a capsule comprising a polyoxyethylene-sorbitan-fatty acid ester, for example polyoxyethylene (20) sorbitan monooleate such as that available under the trade name Tween®80; a reaction product of a natural or hydrogenated castor oil and ethylene oxide, for example polyethylene glycol castor oil such as that available under the trade name Cremophor®RH40 or EL; a sorbitan fatty acid ester, for example Span® 80 (sorbitan monooleate), and ethanol. Hereinafter these cyclosporin compositions with particular reference to the centre fill (e.g. when referring to weights and amounts) are referred to as compositions of the invention.

The capsule composition may be preferably a hard gelatine capsule.

As will be appreciated by a man skilled in the art the present invention extends to variants. For example the compositions of the invention may contain lower alkanols, e.g. propylene glycol and polyethylene glycol.

A cyclosporin-containing composition of the invention in the form of a capsule if desired may comprise:

(a) a hydrophilic surfactant,
(b) a lipophilic component,
(c) a lipophilic surfactant, and
(d) ethanol, characterized by the presence of a polyoxyethylene sorbitan fatty acid ester, a reaction product of a natural or hydrogenated castor oil and ethylene oxide, and a sorbitan fatty acid ester.

It will also be appreciated by a man skilled in the art that the same component may serve as both the lipophilic component and the lipophilic surfactant.

If desired a composition of the invention may be so formulated that on treatment with water it produces a particularly stable emulsion, e.g. microemulsion, or emulsion, e.g. microemulsion.

Compositions of the invention may have particularly interesting bioavailability characteristics and reduced variability in inter- and intra-subject bioavailability parameters. Preferably the composition is in the form of an "emulsion, e.g. microemulsion, preconcentrate" of the type providing o/w (oil-in-water) emulsions, e.g. microemulsions. An "emulsion, e.g. microemulsion, preconcentrate" is defined in this specification as being a composition which spontaneously forms an emulsion, e.g. microemulsion, in an aqueous medium, for example, in water, for example on dilution of the centre fill 1:1 to 1:100, e.g. 1:10, or in the gastric juices after oral application.

A microemulsion is thermodynamically stable and contains dispersed particles of a mean size less than about 200 nm. Generally microemulsions comprise droplets or particles having a mean diameter of less than about 150 nm; typically less than 100 nm, generally greater than 10 nm, and stable over periods in excess of 24 hours. A "microemulsion" may be a non-opaque or substantially non-opaque, alternatively it may be a translucent colloidal dispersion that is formed spontaneously or substantially spontaneously when its components are brought into contact. Further characteristics can be found in British patent application 2 222 770, the disclosure of which is incorporated herein by reference.

In a further aspect the present invention provides a composition of the invention, the relative proportion of the cyclosporin, the lipophilic component, the hydrophilic surfactant, the lipophilic surfactant and the ethanol in said composition being such that upon dilution with water to a ratio of 1 part by weight of said composition centre fill to 1 to 100, e.g. 10 to 100 parts by weight of water, an oil-in-water microemulsion having particles of a mean size of less than 200 nm, is spontaneously formed.

In the centre fill, the cyclosporin may be present in an amount by weight of up to about 20% by weight of the composition of the invention. The cyclosporin is preferably present in an amount of 1 to 15% by weight of the composition of the invention, for example about 2 to 10%.

In a further alternative aspect the lipophilic component may comprise 5 to 35% by weight of the composition centre fill, e.g. 10 to 30%; preferably 15 to 25% by weight, more preferably about 20% or 30% by weight.

In a composition of the invention, in a further alternative aspect the constitutional ratio of the lipophilic component to the cyclosporin is preferably 1–30:1 and more preferably 2–30:1, on the basis of weight.

In a further alternative aspect the hydrophilic surfactant may comprise 25 to 70% by weight of the composition centre fill; preferably 30 to 65% by weight, more preferably 40 to 60% by weight and even more preferably about 50% by weight.

In a composition of the invention, in a further alternative aspect the constitutional ratio of the hydrophilic surfactant to the cyclosporin is preferably 1–60:1 and more preferably 2–60:1, on the basis of weight.

In a further alternative aspect the lipophilic surfactant may comprise 5 to 35% by weight of the composition centre fill, e.g. 5 to 30%; preferably 5 to 20% by weight, more preferably about 10% by weight.

In a composition of the invention, in a further alternative aspect the constitutional ratio of the lipophilic surfactant to the cyclosporin is preferably 1–30:1 and more preferably 2–30:1, on the basis of weight.

In a further alternative aspect the ethanol may comprise 1 to 20% by weight of the composition centre fill, e.g. 5 to 15%; preferably about 10% by weight.

In a composition of the invention, in a further alternative aspect the constitutional ratio of the ethanol to the cyclosporin is preferably 10:1 to 1:10 and more preferably 5:1 to 1:5, on the basis of weight.

In a further aspect the present invention provides a capsule having a composition centre fill comprising 1–20% by weight of Cyclosporin A, 5–35% by weight of a lipophilic component, e.g., Miglyol®812 or Span®80, 25–70% by weight of a hydrophilic surfactant, e.g., Cremophor®RH40 or EL and Tween®80, 5–35% by weight of a lipophilic surfactant, e.g., Span®80, 1–20% by weight of ethanol.

Cyclosporins to which the present invention applies are any of those having pharmaceutical utility, e.g. as immunosuppressive agents, anti-parasitic agents and agents for the reversal of multi-drug resistance, as known and described in the art, in particular Cyclosporin A, Cyclosporin G, [0-(2-hydroxyethyl)-(D)Ser]$^8$-Ciclosporin, and [3'-deshydroxy-3'-keto-MeBmt]$^1$-[Val]$^2$-Ciclosporin. Cyclosporin A is preferred.

In one aspect the present invention provides a composition of the invention wherein the cyclosporin is Cyclosporin A.

Polyoxyethylene-sorbitan-fatty acid esters may comprise for example mono- and tri-lauryl, palmityl, stearyl and oleyl esters of the type known and commercially available under the trade name Tween® from e.g. ICI, UK, including the products Tween®

20[polyoxyethylene(20)sorbitanmonolaurate],
21[polyoxyethylene(4)sorbitanmonolaurate],
40[polyoxyethylene(20)sorbitanmonopalmitate],
60[polyoxyethylene(20)sorbitanmonostearate],
65[polyoxyethylene(20)sorbitantristearate],
80[polyoxyethylene(20)sorbitanronooleate],
81[polyoxyethylene(5)sorbitanmonooleate],
85[polyoxyethylene(20)sorbitantrioleate].

Especially preferred products of this class are Tween®40 (HLB value of about 15 to 16) and Tween®80 (HLB value of about 15).

In the reaction products of a natural or hydrogenated castor oil and ethylene oxide, the natural or hydrogenated castor oil may be reacted with ethylene oxide in a molar ratio of from about 1:35 to about 1:60, with optional removal of the polyethylene glycol component from the products. Various such surfactants are commercially available. The hydrogenated-hydrogenated castor oils available under the trade name Cremophor® are especially suitable. Particularly suitable are Cremophor®RH 40, which has a saponification value of about 50 to 60, an acid value less than about 1, a water content (Fischer) less than about 2%, an $n_D^{60}$ of about 1.453 to 1.457 and an HLB of about 14 to 16; and Cremophor®RH 60, which has a saponification value of about 40 to 50, an acid value less than about 1, an iodine value of less than about 1, a water content (Fischer) of about 4.5 to 5.5%, an $n_D^{60}$ of about 1.453 to 1.457 and an HLB of about 15 to 17. An especially preferred product of this class is Cremophor®RH40. Also suitable are polyethyleneglycol castor oils such as that available under the trade name Cremophor®EL, which has a molecular weight (by steam osmometry) of about 1630, a saponification value of about 65 to 70, an acid value of about 2, an iodine value of about 28 to 32 and an $n_D^{25}$ of about 1.471.

Similar or identical products which may also be used are available under the trade names Nikkol® (e.g. Nikkol® HCO-40 and HCO-60), Mapeg® (e.g. Mapeg® CO-40h), Incrocas® (e.g. Incrocas® 40), Tagat® (for example polyoxyethylene-glycerol-fatty acid esters e.g. Tagat® RH 40; and Tagat® TO, a polyoxyethylene-glycerol-trioleate having a HLB value of 11.3; Tagat® RH 40 is preferred) and Simulsol OL-50 (PEG-40 castor oil, having a saponification value of about 55 to 65, an acid value of max. 2, an iodine value of 25 to 35, a water content of max. 8%, and an HLB of about 13, available from Seppic). These surfactants are further described in Fiedler "Lexikon der Hilfsstoffe für Pharmazie, Kosmetik und angrenzende Gebiete", Editio Cantor Verlag Aulendorf, Aulendorf, 4th revised and expanded edition (1996), and "Handbook of Pharmaceutical Excipients", 2nd Edition, Editors A. Wade and P. J. Weller (1994), Joint publication of American Pharmaceutical Association, Washington, USA and The Pharmaceutical Press, London, England.

The polyoxyethylene-sorbitan-fatty acid ester and the reaction product of a natural or hydrogenated castor oil and ethylene oxide may e.g comprise 25–70% by weight of the centre fill.

Preferred sorbitan fatty acid esters include sorbitan mono $C_{12-18}$ fatty acid esters, or sorbitan tri $C_{12-18}$ fatty acid esters as known and commercially available under the trade mark Span® from e.g. ICI. An especially preferred product of this class is e.g. Span®20 (sorbitan monolaurate, HLB value of about 8) or Span®80 (sorbitan monooleate, HLB value of about 4) (Fiedler, loc. cit., 2, p. 1430; Handbook of Pharmaceutical Excipients, loc. cit., page 473).

The sorbitan fatty acid esters may e.g comprise 10–70% by weight of the centre fill. Examples of polyalkylene glycol materials are polyethylene glycols, in particular polyethylene glycols having a molecular weight of from ca. 500 to ca. 4,000, e.g. from ca. 1,000 to ca. 2,000.

In a further alternative aspect of the invention there are a plurality of alkanols. For example the ethanol may be replaced or partially replaced by an alkanol which may be hydrophilic, e.g. selected from Transcutol (which has the formula $C_2H_5$—[O—$(CH_2)_2$]$_2$—OH), Glycofurol (also known as tetrahydrofurfuryl alcohol polyethylene glycol ether), and 1,2-propylene glycol.

Quantities of liquid and/or solid polyethylene glycols, e.g. polyethylene glycol (PEG) 3350 or PEG 1450, as known and commercially available from e.g. Union Carbide, USA, may also be included in the composition of the invention.

GB 2 222 770 A discloses a wide variety of lipophilic components suitable for use in a composition of the invention. Typical examples for lipophilic components are:

(i) medium chain fatty acid triglycerides, e.g. $C_6$–$C_{12}$, e.g. Miglyol® 812, and/or (ii) mixed mono-, di-, tri-glycerides, e.g. $C_6$–$C_{20}$, e.g. $C_{16}$–$C_{18}$, e.g. Maisine®, and/or (iii) transesterified ethoxylated vegetable oils, e.g. Labrafil®, and/or (iv) propylene glycol mono fatty acid esters, e.g. $C_{14}$–$C_{18}$, e.g. propylene glycol hydroxystearate, propylene glycol isostearate, propylene glycol ricinoleate, propylene glycol stearate, and/or (v) propylene glycol di fatty acid esters, e.g. $C_6$–$C_{20}$, e.g. $C_8$–$C_{12}$, e.g. propylene glycol dicaprylate, e.g. Miglyol® 840, or propylene glycol dilaurate, and/or (vi) esterified compounds of fatty acid and primary alcohol, e.g. $C_8$–$C_{20}$ fatty acids and $C_2$–$C_3$ alcohols, e.g. ethyl linoleate, and/or (vii) mono- and/or di-glyceride, e.g. a mixture of mono- and di-glycerides with e.g. a monoglyceride of $C_{18}$ fatty acid as its main component, e.g. GMOrphic®-80 or Tegin® O.

Preferred lipophilic components are medium chain fatty acid triglycerides, mixed mono-, di-, tri-glycerides, sorbitan fatty acid esters and transesterified ethoxylated vegetable oils. Accordingly, in one aspect the present invention provides a composition of the invention wherein the lipophilic component is a medium chain fatty acid triglyceride, or a sorbitan fatty acid ester.

In another aspect the lipophilic component may comprise a medium chain triglyceride and/or a mono- and di-glyceride or a mixture thereof.

As the medium chain fatty acid triglyceride in the lipophilic component a triglyceride of saturated fatty acid having 6 to 12, e.g. 8 to 10, carbon atoms can be used. Suitable medium chain fatty acid triglycerides are those known and commercially available under the trade names Acomed®, Myritol®, Captex®, Neobee®M 5 F, Miglyol®810, Miglyol®812, Miglyol®818, Mazol®, Sefsol®860, Sefsol®870; Miglyol®812 being the most preferred. Miglyol®812 is a fractionated coconut oil comprising caprylic-capric acid triglycerides and having a molecular weight of about 520 Daltons. Fatty acid composition=$C_6$ max. about 3%, $C_8$ about 50 to 65%, $C_{10}$ about 30 to 45%, $C_{12}$ max 5%; acid value about 0.1; saponification value about 330 to 345; iodine value max 1. Miglyol® 812 is available from Condea. Neobee® M 5 F is a fractionated caprylic-capric acid triglyceride available from coconut oil; acid value max. 0.2; saponification value about 335 to 360; iodine value max 0.5, water content max. 0,15%, $D.^{20}$ 0,930–0,960, $n_D^{20}$ 1,448–1, 451 (manufacturer information). Neobee® M 5 F is available from Stepan Europe.

These triglycerides are described in Fiedler, H. P., loc cit, the contents of which are hereby incorporated by reference.

In a further alternative aspect triglycerides suitably comprise at least 5% but less than about 25%, based on the total weight of the lipophilic component. More preferably from about 7.5 to about 20% (for example from about 9 to 12%) triglycerides are present.

Suitable mixed mono-, di-, tri-glycerides are those known and commercially available under the trade name Maisine® from Gattefossé. They are transesterification products of corn oil and glycerol.

In a composition of the invention, in a further alternative aspect the constitutional ratio of the lipophilic component to cyclosporin is preferably 1–30:1 and more preferably 2–30:1, on the basis of weight.

It is to be appreciated that the components may be complex mixtures containing side products or unreacted starting products involved in the preparation thereof, e.g. surfactants made by polyoxyethylation may contain another side product, e.g. polyethylene glycol.

A surfactant having a hydrophilic-lipophilic balance (HLB) value of 8 to 17 is conveniently present. The HLB value is preferably the mean HLB value.

According to the invention a hydrophilic surfactant may be mixed with a lipophilic surfactant. Under a hydrophilic surfactant is to be understood a surfactant having an HLB value of greater than or equal to 10, whereas under a lipophilic surfactant is to be understood a surfactant having an HLB value of less than 10.

A hydrophilic surfactant selected preferably has a hydrophilic-lipophilic balance (HLB) of greater than or equal to 10, for example Cremophor®RH40 or EL.

One component selected preferably has a hydrophilic-lipophilic balance (HLB) of less than 10, for example Span®80.

If desired the relative proportion of the lipophilic components, the surfactants and the ethanol lie within the "microemulsion" region on a standard three-way plot. The compositions thus obtained are microemulsion preconcentrates of high stability that are capable, on addition to water, of providing microemulsions having a mean particle size of <200 nm.

Standard three way plots, e.g. phase diagrams, can be generated in a conventional manner as described in e.g. GB patent publication no. 2 222 770 or WO 96/13273.

The emulsion, e.g. microemulsion, preconcentrate compositions, e.g. those in the examples hereinafter, may show good stability characteristics as indicated by standard stability trials, for example having a shelf life stability of up to one, two or three years, and even longer. The microemulsion preconcentrate compositions of this invention produce stable microemulsions, e.g. for up to one day or longer, e.g. one day.

The composition of the invention may also include further additives or ingredients, for example antioxidants (such as ascorbyl palmitate, butyl hydroxy anisole (BHA), butyl hydroxy toluene (BHT) and tocopherols) and/or preserving agents. In a further alternative aspect these additives or ingredients may comprise about 0.05 to 1% by weight of the total weight of the composition centre fill. The composition of the invention may also include sweetening or flavoring agents in an amount of up to about 2.5 or 5% by weight based on the total weight of the composition centre fill. Preferably the antioxidant is α-tocopherol (vitamin E).

Details of excipients for use in a composition of the invention are described in Fiedler, H. P., loc cit; "Handbook of Pharmaceutical Excipients", loc cit; or may be obtained from the relevant manufacturers, the contents of which are hereby incorporated by reference.

Any carbon chain not otherwise specified herein conveniently contains 1 to 18 carbon atoms, e.g. 10 to 18 carbon atoms, when a terminal group or 2 or 3 carbon atoms when a polymer moiety.

The compositions of the invention exhibit especially advantageous properties when administered orally; for example in terms of consistency and high level of bioavailability obtained in standard bioavailability trials, e.g. 2 to 4 times higher than known emulsions. These trials are performed in animals e.g. rats or dogs or healthy volunteers using HPLC or a specific or nonspecific monoclonal kit to determine the level of the cyclosporin in the blood. For example, the composition of Example 1 administered p.o. to dogs may give surprisingly high $C_{max}$ values as detected by ELISA using a specific monoclonal antibody. In one aspect the present invention provides a method of orally administering a pharmaceutical composition, said method comprising orally administering to a patient in need of cyclosporin therapy a composition of the invention.

Pharmacokinetic parameters, for example absorption and blood levels, also become surprisingly more predictable and problems in administration with erratic absorption may be eliminated or reduced. Additionally the compositions of the invention are effective with tenside materials, for example bile salts, being present in the gastro-intestinal tract. That is, the compositions of the invention are fully dispersible in aqueous systems comprising such natural tensides and thus capable of providing microemulsion systems in situ which are stable and do not exhibit precipitation of the active agent or other disruption of fine particulate structure. The function of the compositions of the invention upon oral administration remain substantially independent of and/or unimpaired by the relative presence or absence of bile salts at any particular time or for any given individual.

The compositions of the invention reduce variability in inter- and intra-patient dose response.

In one aspect the present invention provides a method of reducing the variability of bioavailability levels of a cyclosporin for patients during cyclosporin therapy, said method comprising orally administering an oral pharmaceutical composition according to the present invention.

In a further alternative aspect the invention also provides a process for the production of a composition of the invention, which process comprises bringing cyclosporin, ethanol and other components into intimate admixture. When required, the composition may be compounded into unit dosage form, for example filling the composition into gelatine capsules.

Optionally further components or additives may be mixed with the components with or after addition of active agent.

The composition may be combined with water or an aqueous solvent medium such that an emulsion, e.g. microemulsion, is obtained.

The utility of all the pharmaceutical compositions of the invention may be observed in standard clinical tests in, for example, known indications of cyclosporin using dosages giving equivalent blood levels of cyclosporin; for example using dosages in the range of 2.5 mg to 1000 mg of active agent per day for a 75 kilogram mammal, e.g. adult and in standard animal models. The increased bioavailability of the cyclosporin provided by the compositions may be observed in standard animal tests and in clinical trials, e.g. as described above.

The optimal dosage of cyclosporin to be administered to a particular patient must be considered carefully as individual response to and metabolism of the cyclosporin may vary. It may be advisable to monitor the blood serum levels of the active agent by radioimmunoassay, monoclonal antibody assay, or other appropriate conventional means. Cyclosporin dosages may be e.g. 25 to 1000 mg per day (preferably 50 mg to 500 mg)

The compositions of the invention are preferably compounded in unit dosage form, for example by filling them into orally administrable capsule shells. The capsule shells may be soft or hard gelatine capsule shells. Where the composition of the invention is in unit dosage form, each unit dosage will suitably contain between 10 and 100 mg of the cyclosporin, more preferably between 10 and 50 mg; for example 15, 20, 25, or 50 mg. Such unit dosage forms are suitable for administration 1 to 5 times daily depending upon the particular purpose of therapy, the phase of therapy and the like.

However, if desired, the compositions of the invention may be in drink solution form and may include water or any other aqueous system, to provide emulsion, e.g. microemulsion, systems suitable for drinking.

The compositions of the invention are particularly useful for:
- a) treatment and prevention of organ or tissue transplant rejection, for example for the treatment of the recipients of heart, lung, combined heart-lung, liver, kidney, pancreatic, skin or corneal transplants. The compositions of the invention are also indicated for the prevention of graft-versus-host disease, such as sometimes occurs following bone marrow transplantation;
- b) treatment and prevention of autoimmune disease and of inflammatory conditions, in particular inflammatory conditions with an aetiology including an autoimmune component such as arthritis (for example rheumatoid arthritis, arthritis chronic progrediente and arthritis deformans) and rheumatic diseases; and
- c) treatment of multi-drug resistance (MDR).

In a further aspect the present invention provides the use of a composition of the invention in the manufacture of a medicament for the treatment and prevention of an autoimmune or inflammatory condition or for the treatment and prevention of transplant rejection or for the treatment of multi-drug resistance.

EXAMPLES

Following is a description by way of example only of compositions of the invention. Unless otherwise indicated, components are shown in % by weight based on each composition centre fill.

Miglyol®812 is from the Condea Company, Germany.
Cremophor®RH 40 is from BASF, Germany.
Span®80 is from ICI, UK.
Tween®80 is from ICI, UK.

Example 1

A composition is made up with the following components:
40% by volume of a Cremophor®RH40
32% by volume of a Miglyol®812
8% by volume of Span®80
10% of volume cyclosporin A
10% of volume ethanol Example 2

A composition is made up with the following components:
56% by weight of Cremophor®EL
16% of Miglyol®812
8% of Span®80
10% of cyclosporin A
10% of ethanol Other Examples may be made by omitting Miglyol®812 and replacing the Miglyol®812 by Span®80.

Further Examples may be made by replacing part (e.g. 30 to 70%) of the Cremophor®EL by an equivalent amount of Tween®80.

These compositions may be encapsulated in hard and soft gelatine capsules.

The examples illustrate compositions useful for example in the prevention of transplant rejection or for the treatment of autoimmune disease, on administration of from 1 to 5 unit dosages/day at a dose of 2 to 5 mg/kg per day.

On visual inspection after dilution, each of the compositions may form a clear and stable microemulsion or emulsion.

What is claimed is:

1. A cyclosporin-containing composition in the form of a capsule comprising a polyoxyethylene sorbitan fatty acid ester, a reaction product of a natural or hydrogenated castor oil and ethylene oxide, a sorbitan fatty acid ester, and ethanol.

2. A cyclosporin-containing composition in the form of a capsule comprising:
    (a) a hydrophilic surfactant,
    (b) a lipophilic component,
    (c) a lipophilic surfactant, and
    (d) ethanol,
characterized by the presence of a polyoxyethylene sorbitan fatty acid ester, a reaction product of a natural or hydrogenated castor oil and ethylene oxide, and a sorbitan fatty acid ester.

3. A hard gelatin capsule containing the composition of claim 1.

4. A composition according to claim 1 comprising the cyclosporin in an amount of 1 to 20% by weight of the composition center fill.

5. A composition according to claim 2 comprising the lipophilic component in an amount of 5 to 35% by weight of the composition center fill.

6. A composition according to claim 2 comprising the hydrophilic surfactant in an amount of 25 to 70% by weight of the composition center fill.

7. A composition according to claim 2 comprising the lipophilic surfactant in an amount of 5 to 35% by weight of the composition center fill.

8. A composition according to claim 1 comprising the ethanol in an amount of 1 to 20% by weight of the composition center fill.

9. A composition according to claim 1 wherein the cyclosporin is Cyclosporin A.

10. A composition according to claim 1 wherein a hydrophilic co-component is present.

11. A method of reducing of variability of bioavailability levels of a cyclosporin for patients during cyclosporin therapy, said method comprising orally administering a composition according to claim 1.

12. A method of orally administering a pharmaceutical composition, said method comprising orally administering to a patient in need of cyclosporin therapy a composition according to claim 1.

13. A method of 1) treating and preventing an autoimmune or inflammatory condition, 2) treating and preventing transplant rejection, or 3) treating multi-drug resistance, which comprises administering to a person in need thereof an effective amount of a composition of claim 1.

14. A process for the production of a composition according to claim 1, which process comprises bringing cyclosporin and ethanol into intimate admixture.

* * * * *